United States Patent [19]

Rubin et al.

[11] Patent Number: 4,490,523

[45] Date of Patent: Dec. 25, 1984

[54] MANDELONITRILE TRIACETYL GLUCURONATE AND PROCESS FOR PREPARING SAME

[75] Inventors: Ely J. Rubin, 5 Rav Zair, Jerusalem, Israel; Israel Shahak, Jerusalem, Israel

[73] Assignees: Ely J. Rubin; David Rubin, both of Jerusalem, Israel; Century Science Corp., Port Washington, N.Y.

[21] Appl. No.: 320,086

[22] Filed: Nov. 10, 1981

[51] Int. Cl.$^3$ .............................................. C07H 5/10
[52] U.S. Cl. .................................. 536/4.1; 536/17.1; 536/18.2; 536/18.5
[58] Field of Search ............... 536/4, 4.1, 18.2, 18.5, 536/17.1

[56] References Cited

U.S. PATENT DOCUMENTS

| | | | |
|---|---|---|---|
| 2,845,439 | 7/1958 | Reiners | 536/4 |
| 2,985,664 | 5/1961 | Krebs et al. | 536/4 |
| 3,959,253 | 5/1976 | Jones | 536/4 |
| 4,335,236 | 6/1982 | Tsuyumu et al. | 536/4 |

FOREIGN PATENT DOCUMENTS

| | | |
|---|---|---|
| WO80/791 | 5/1980 | PCT Int'l Appl. |
| 788855 | 1/1958 | United Kingdom |

OTHER PUBLICATIONS

"5548, Mandelonitrile Glucoside" *Merck Index*, 9th edition, p. 743, (1976).

Hurst, D. T. et al., "The Alcoholysis of Trialkylalkoxysilanes" *Can. J. of Chem.*, 43, 2004–2011, (1965).

Helferich, B. et al., "Zur Synthese von Disacchariden IV, Zwei Tetra-Acetyl-Beta-D-Glucosen", *Annalen der Chemie*, 450, pp. 219–229, (1926).

Stacey, M., "The Synthesis of Uronic Acids", *J. Chem. Soc.*, pp. 1529–1531, (1939).

Progress Reports No. 28–33, Merck Sharp & Dohme Research Laboratories, "Quarterly Project Report to Cancer Chemotherapy National Service Center, Contract PH–43–62–479", Jan. 1965 through Jun. 1966.

Fenselau, C., "Mandelonitrile Beta-Glucuronide: Synthesis and Characterization", *Science*, 198 (4317), 625–627.

Schaudbury, D. N. et al., "The Synthesis of Gein and of the Hexa-acetyl Beta-Vicianoside of (−)-Mandelonitrile Believed to be the Hexa-acetate of Vicianin", *J. Chem. Soc.*, 1949, 2054–2057, (1949).

*Primary Examiner*—Johnnie R. Brown
*Attorney, Agent, or Firm*—Browdy and Neimark

[57] ABSTRACT

Mandelonitrile-β-D-glucuronic acid can be produced by tritylating mandelonitrile-β-D-glucoside, acetylating the obtained product, and then simultaneously detritylating and oxidizing in order to obtain mandelonitrile-β-D-triacetyl glucuronic acid. This compound may then be deacetylated to obtain mandelonitrile-β-D-glucuronic acid or the salt thereof.

4 Claims, No Drawings

MANDELONITRILE TRIACETYL GLUCURONATE AND PROCESS FOR PREPARING SAME

CROSS REFERENCE TO RELATED APPLICATION

The present application is related to application Ser. No. 951,270, filed Oct. 13, 1978, to one of the present inventors, concerning another method for the production of mandelonitrile-β-D-glucuronic acid and application Ser. No. 951,269, filed Oct. 13, 1978 to one of the present inventors which relates to another method for the production of conjugates of free glucuronic acid with aglycones which are strong electron acceptors.

FIELD OF THE INVENTION

The present invention relates to novel methods of making glucuronide compounds the aglycones of which are strong electron acceptors, and more particularly, to a novel process for the synthesis of mandelonitrile-β-D-glucuronic acid.

BACKGROUND OF THE INVENTION

It has been suggested in British Pat. No. 788,855 that mandelonitrile-β-D-glucuronic acid may be used in the treatment of malignant tumors as β-glucuronidase is prevalent in malignant tissues and this enzyme will selectively attack mandelonitrile-β-D-glucuronic acid at the site of the malignant tumors to split off hydrogen cyanide. U.S. Pat. No. 2,985,664 is also related to mandelonitrile-β-D-glucuronic acid and a method of producing same.

It has been discovered, however, that none of the methods of producing this compound set forth in the above mentioned patents are reproducible. Attempts to oxidize prunisin by the methods described by Krebs produce the glucuronide of mandelic acid because the CN group is unstable. Attempts to condense mandelonitrile with glucuronic acid or glucuronolactone or tetraacetylglucuronolactone halogenide have failed because the mandelonitrile tends to polymerize.

In 1966, Merck Pharmaceutical Company was requested by the U.S. National Institutes of Health to duplicate the synthesis of this compound as taught by the Krebs patents. In a series of quarterly progress reports to the Cancer Chemotherapy National Service Center, Merck, Sharpe & Dohme Research Laboratories reported that none of the methods disclosed in either of the above mentioned Krebs patents could be duplicated. The Merck reports specified that while amygdalin can be hydrolyzed to mandelonitrile-β-D-glucoside (although by acid hydrolysis rather than enzymatic hydrolysis), none of the desired material could be obtained from catalytic air oxidation of the glucoside as taught by the Krebs patents. They were further unable to repeat the Krebs directions for total synthesis by condensing d,l-mandelonitrile with β-glucuronic acid.

The Merck report details many unsuccessful efforts which were made to oxidize the mandelonitrile-β-D-glucoside to the corresponding mandelonitrile-β-D-glucuronic acid. It has specified, however, that the formation of any detectable amount of the desired product was never demonstrated in spite of many variations in conditions and catalysts either using Krebs recommended catalyst, "platinum black," or other catalysts, including platinum or palladium on charcoal, platinum oxide, Adam's catalyst, or certain specially prepared sugar oxidation catalysts.

The Merck report also reported on attempted chemical oxidation of the glucoside to the glucuronic acid by first preparing the 6-trityl derivative of the glucoside followed by acetylation and removal of the 6-tritylgroup in refluxing 80% aqueous acetic acid. It is reported that several chemical oxidation agents, such as potassium permanganate and chromic acid were tried giving a dark oily product, from which no useful material was obtained. It was further reported that catalytic air oxidation on this triacetate also gave back the starting material.

The only method discovered by Merck to be even partially successful in producing the desired glucuronic acid entailed oxidation with liquid nitrogen dioxide of the unprotected monoglucoside. The results were so poor however, that only a 6.5% yield could be obtained (less than 0.5 g) after several recrystallizations.

Fenselau et al in *Science*, 198 (4317) 625–627, 1977, reported that no successful synthesis of mandelonitrile glucuronide has been reported since the original Krebs patents. Furthermore, they report that since the original Krebs processes had not been reproduced, they proceeded to develop their own synthesis of mandelonitrile glucuronide using UDP-glucuronosyl transferase immobilized on beaded Sepharose.

In PCT application WO 80/00791 a method of synthesis of mandelonitrile-β-D-glucuronic acid was described which comprises first reacting mandelic acid with gaseous ammonia to form a reaction product, and then reacting with the methyl (tri-O-acetyl β-D-glucopyranosyl) bromide uronate to produce methyl ester of the corresponding glucuronic acid. This compound may then be mixed with acetic anhydride to convert the mandelic acid-ammonia reaction product to mandelonitrile. Treatment with barium hydroxide and sulfuric acid will then produce the mandelonitrile-β-D-glucuronic acid. However, this method has a yield of only about 30%.

It is thus clear that the synthesis of mandelonitrile-β-D-glucuronic acid has been very difficult and cannot be accomplished by conventional techniques in any kind of a desirable yield.

PCT international publication WO 80/00791, the entire contents of which are hereby incorporated by reference, discloses significant utilities for mandelonitrile-β-D-glucuronic acid including antibacterial activity against bacterial infections by bacteria which are known to have high β-glucuronidase activity and against certain tumors which have high β-glucuronidase activity.

SUMMARY OF THE INVENTION

Accordingly, it is an object of the present invention to overcome the deficiencies of the prior art.

It is another object of the present invention to provide for a method for the totally chemical synthesis of mandelonitrile-β-D-glucuronic acid in high yields.

These and other objects of the present invention will be better understood from a reading of the following summary and the detailed description of the present invention.

D-mandelonitrile-glucoside (prunasin) may be oxidized to mandelonitrile glucuronic acid, after first tritylating and acetylating in accordance with well known procedures by simultaneously detritylating and oxidizing to obtain the mandelonitrile triacetyl glucuronic acid, followed by deacetylation. It has been discovered that the detritylation and oxidation steps must be accomplished simultaneously in order to permit the oxidation to take place. As discussed hereinabove, the Merck report indicates that if the compound is first detritylated, as would be the conventional procedure, the oxidation will not take place, as only dark oily products will be produced from which no useful material can be obtained.

A classical method of selectively reacting the primary alcohol groups of sugars without affecting the remaining hydroxyl groups is to first tritylate the sugar. Triphenylmethyl chloride (also known as trityl chloride) in the presence of pyridine reacts with the primary alcohol groups of sugars to give triphenylmethyl ethers, a process frequently called tritylation, in accordance with the following reaction scheme:

$$RCH_2OH + ClC(C_6H_5)_3 + C_5H_5N \rightarrow RCH_2OC(C_6H_5)_3 + C_5H_5NHCl.$$

The remaining hydroxyl groups can then be acetylated. In the classical procedure, the triphenylmethyl group is then selectively removed since triphenylmethyl ethers are hydrolyzed more readily in acid solution than are methyl esters. With the remaining hydroxyl groups protected by the acetyl groups the primary alcohol group can then be selectively reacted. Such procedure is known, for example, from D. N. Schaudhury et al, *J. Chem. Soc.*, 1949, 2054; Hurst, D. T. et al, *Can. J. of Chem.*, 43, 2004 (1965); Helferidge, C. H. An., 450, 219, (1926); and Stacey, M., *J. Chem. Soc.*, 1939, 1529.

It has unexpectedly been discovered that the oxidation step from the glucoside to the glucuronide can proceed at high yield if it is accomplished simultaneously with detritylation, in statu nascendi. A relatively mild oxidizing agent should be used under relatively mild conditions in order to avoid damage to the nitrile group or hydrolysis of the glucuronide. Preferably, the tritylated and acetylated glucoside is dissolved in glacial acetic acid and magnesium bichromate and then refluxed until the reaction is complete. Alternatively, the product may be dissolved in acetone with concentrated sulfuric acid and magnesium bichromate gradually added thereafter, while keeping the temperature down to 0°–10° C. Sodium bichromate may also be used as the oxidizing agent in place of magnesium bicarbonate.

The obtained triacetyl mandelonitrile glucuronide is then treated to remove the protecting groups. As disclosed in said PCT publication WO 80/00791, this is also a very difficult operation because of the instability of the nitrile group. One method of deacetylating is to treat the product with barium hydroxide to produce a white precipitate and then treat the precipitate with a sufficient quantity of sulfuric acid until precipitation of barium sulfate is completed. The supernatant contains the mandelonitrile-β-D-glucuronic acid.

Alternatively, and preferably, the acetylation can also be accomplished by ammonolysis in warm methanol.

The discovery of the present invention is that oxidation of the mandelonitrile glucoside to the mandelonitrile glucuronic acid can only be accomplished if the detritylation and the oxidation steps are conducted simultaneously. The specific reagents and reaction conditions for the various steps are not critical, and it can be readily determined by anyone of ordinary skill in the art with no more than routine experimentation. Preferred reagents and reaction conditions are described herein, but the present invention is not limited to these preferred reagents and conditions as long as the critical step of simultaneous detritylation and oxidation is used.

Furthermore, while tritylation is used in order to protect the primary alcohol group of the glucoside, it should be understood that compounds similar to triphenylmethyl chloride can be used place thereof. For example, it would be expected that tri-paramethoxy triphenylphosphene would be equally protective of the primary alcohol group. Another glucoside group at the site of the primary alcohol may also serve the same function. Thus, amygdalin, after being acetylated, may be simultaneously hydrolyzed and oxidized in order to directly produce the glucuronic acid without first being hydrolyzed into the monoglucoside.

DESCRIPTION OF PREFERRED EMBODIMENTS

EXAMPLE I

Formation of trityl prunasin triacetate

Mandelonitrile-β-D-glucuronic acid may be synthesized, in accordance with the present invention, starting with prunasin (D-mandelonitrile glucoside). This may be obtained by enzymatic or acid hydrolysis of amygdalin in accordance with well known techniques. See *Merck Index*, 9th edition, page 743, "5548. Mandelonitrile glucoside".

60 g of prunasin is dissolved in 250 ml of dimethyl formamide. Dimethyl acetamide may be substituted for dimethyl formamide. 60 g of triphenylmethyl chloride and 100 cc pyridine are added and stirred overnight at room temperature to form trityl prunasin in accordance with reaction I. After 24 hours, 30 cc of pyridine and 90 ml acetic anhydride are added and stirred for another 24 hours at room temperature to form the trityl prunasin triacetate in accordance with reaction II.

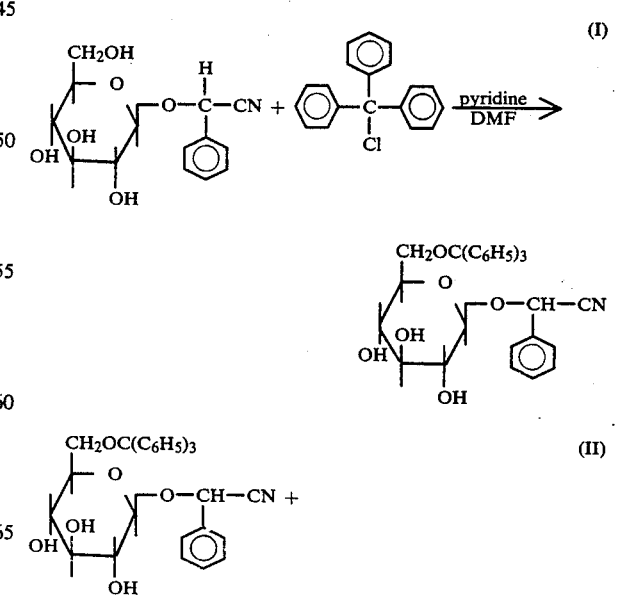

-continued

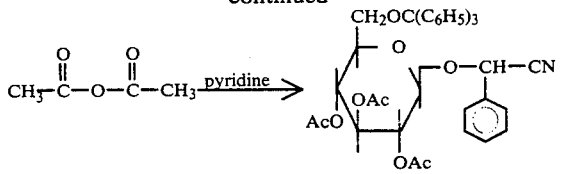

EXAMPLE II

Formation of mandelonitrile triacetyl glucuronic acid 6.6 g of trityl prunasin triacetate obtained in accordance with example I are dissolved in 60 g glacial acetic acid and 4 g of magnesium bichromate and then refluxed for 5–10 minutes. Simultaneous detritylation and oxidation takes place yielding the mandelonitrile triacetyl glucuronide in high yield, in accordance with Reaction III.

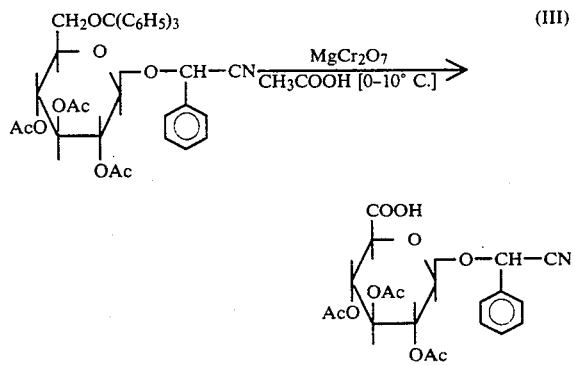

EXAMPLE III

Alternative method of preparing mandelonitrile triacetyl glucuronic acid

Into 6.6 g of trityl prunasin triacetate prepared in accordance with example I, in 50 ml of acetone, portions of concentrated sulfuric acid to the total of 10 cc and portions of magnesium bichromate to the total of 4 g are gradually added one after the other, while stirring. The temperature should be kept continuously at the range of 0°–10° C. The temperature should not be allowed to rise above 10° C. Mandelonitrile triacetyl glucuronic acid is obtained in high yield.

EXAMPLE IV

Production of mandelonitrile glucuronic acid

The mandelonitrile triacetyl glucuronic acid obtained in accordance with Example II or III is poured onto 300 cc of ice water and then extracted with a total of 200 cc methylene chloride and separated. The methylene chloride solution is extracted with sodium bicarbonate-water solution which yields the sodium salt of the triacetyl mandelonitrile glucuronide. This compound is salted out with either $H_2SO_4$ or HCl at pH levels between 3 and 4 to yield the free protected acid.

The protected acid (mandelonitrile triacetyl glucuronic acid) is crystallized from 1:9 water-methanol solution. The removal of the protecting acetyl groups is done by ammonolysis, in accordance with reaction IV. 220 g of the protected acid is dissolved in 400 cc of warm methanol and 200 cc of concentrated ammonia is added in portions, while stirring. After 24 hours, the ammonia and methanol are evaporated. In order to crystallize, the above should be evaporated to dryness and then dissolved at 400 ml of isopropanol and 40 cc of distilled water and left overnight in a refrigerator. The total yield of mandelonitrile glucuronic acid is about 70% based on the starting prunasin. It should be noted that when the protecting acetyl groups are removed by ammonolysis, the ammonium salt of mandelonitrile glucuronic acid is obtained, which is in fact desirable for eventual treatment as this causes the compound to have the proper pH for intervenous administration.

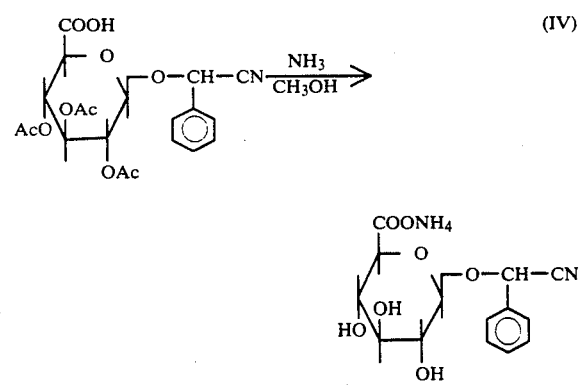

It should be understood that the magnesium bichromate used in examples II and III may be substituted by sodium bichromate, although the former is preferred as it is soluble in acetone.

As stated hereinabove, the particular reagents are not critical. For example, any known mild oxidizing agent may be used, such as calcium oxide, zinc oxide, etc. Only routine experimentation need be utilized in order to determine whether any given oxidizing agent is sufficiently mild to render the process operable.

It will be obvious to those skilled in the art that various changes may be made without departing from the scope of the invention and the invention is not to be considered limited to what is described in the specification.

What is claimed is:

1. A method for the production of mandelonitrile-β-D-glucuronic acid, comprising:
   tritylating mandelonitrile-β-D-glucoside to produce mandelonitrile-β-D-trityl glucoside;
   acetylating the obtained mandelonitrile-β-D-trityl glucoside to obtain mandelonitrile-β-D-triacetyl tritylglucoside;
   simultaneously detritylating and oxidizing the mandelonitrile-β-D-triacetyl trityl glycoside by reacting with an oxidizing agent in the presence of an acid, under conditions and using agents sufficiently mild to obtain mandelonitrile-β-D-triacetyl glucuronic acid; and
   deacetylating the obtained mandelonitrile-β-D-triacetyl glucuronic acid to obtain mandelonitrile-β-D-glucuronic acid or a salt thereof.

2. Mandelonitrile triacetyl glucuronic acid, said compound having the formula:

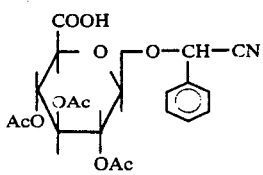

wherein Ac is an acetyl moiety.

3. The method of making the compound in accordance with claims 2, comprising:

tritylating mandelonitrile-β-D-glucoside to produce mandelonitrile-β-D-trityl glucoside;

acetylating the obtained mandelonitrile-β-D-trityl glucoside to obtain mandelonitrile-β-D-triacetyl tritylglucoside; and simultaneously detritylating and oxidizing the mandelonitrile-β-D-triacetyl trityl glycoside by reacting with an oxidizing agent in the presence of an acid, under conditions and using agents sufficiently mild to obtain mandelonitrile-β-D-triacetyl glucuronic acid.

4. A method for the production of mandelonitrile-β-D-glucuronic acid, starting with a mandelonitrile-β-D-glucoside the primary alcohol group of which has been protected by means of a protecting group capable of selectively reacting with said primary alcohol group, said protecting group being selected from the group consisting of triphenylmethyl chloride, tri-paramethoxy triphenylphosphene and a glucoside moiety, comprising:

acetylating the remaining hydroxyl groups of the protected mandelonitrile-β-D-glucoside;

simultaneously removing the protecting group and oxidizing the primary alcohol to the corresponding acid under conditions and using deprotecting and oxidizing agents sufficiently mild to obtain mandelonitrile-β-D-triacetyl glucuronic acid; and deacetylating the obtained mandelonitrile-β-D-triacetyl glucuronic acid to obtain mandelonitrile-β-D-glucuronic acid or a salt thereof.

* * * * *

UNITED STATES PATENT AND TRADEMARK OFFICE
CERTIFICATE OF CORRECTION

PATENT NO. : 4,490,523

DATED : December 25, 1984

INVENTOR(S) : RUBIN et al

It is certified that error appears in the above-identified patent and that said Letters Patent is hereby corrected as shown below:

[75] Inventors: Ely J. Rubin; Israel Shahak; David Rubin, all of Jerusalem, Israel Signed and Sealed this Twenty-third Day of April 1985

[SEAL]

Attest:

DONALD J. QUIGG

*Attesting Officer*     *Acting Commissioner of Patents and Trademarks*